US00PP08434P

United States Patent [19]

Watlington

[11] Patent Number: Plant 8,434

[45] Date of Patent: Oct. 26, 1993

[54] GRAPVINE, NAMED 'VALPLATINTA'

[75] Inventor: Francisco Watlington, Santurce, P.R.

[73] Assignee: Commonwealth of Puerto Rico, San Juan, P.R.

[21] Appl. No.: 786,516

[22] Filed: Nov. 1, 1991

[51] Int. Cl.[5] ..... A01H 5/00

[52] U.S. Cl. ..... Plt./47.1

[58] Field of Search ..... Plt./47.1, 47.2

*Primary Examiner*—James R. Feyrer

*Attorney, Agent, or Firm*—Oblon, Spivak, McClelland, Maier & Neustadt

[57] ABSTRACT

Description of a new and distinct grapevine cultivar: Valplatinta, originated from seed of a hand-pollinated cross of IAC-823-47 (non-patented) by Esperanza (non-patented) is provided. This new variety combines the native adaptation of *Vitis caribaea* to the tropical zone, and desirable attributes for juice and wine making of European (*V. vinifera*) and American (Labruscana) cultivars.

2 Drawing Sheets

BACKGROUND OF THE INVENTION

Although the cultivated grape (*Vitis vinifera* L.) is not a tropical plant, commercial viticulture is on the increase in many tropical areas. The diminished productivity of introduced higher latitude cultivars is offset by the possibility of two crops in one year. However, lack of adaptedness to relatively short day-lengths and high humidity generally results in fruit of poor quality.

By and large, available non-tropical grape varieties commonly suffer delayed, incomplete and irregular ripening, attended by inadequate levels of sugar, acidity and color. This can be compounded by cracking and rotting of unripe berries following rain. Foliage and developing fruit of *vinifera* type grapes are especially susceptible to various mildews and other fungus maladies in tropical environments.

Remedial techniques such as the use of growth regulators to increase budbreak, loosen clusters and improve ripening, as well as intensive spray schedules with fungicides, are costly imperatives that keep tropical viticulture from becoming competitive in the world market. Alternatively, the development of better adapted grape varieties through selective hybridization with native tropical species is a promising approach not widely practiced because of the considerable time-span required to raise and evaluate a single generation of hybrid progeny. The invention is an early product of a research and development program begun in 1966.

GENETIC BACKGROUND

Valplatinta is a hybrid of IAC 823-47 (non-patented seed parent) by Esperanza (non-patented pollen parent). IAC 823-47 is a functionally female tropical hybrid grape selection developed for breeding purposes by J. A. Santos-Neto at the Instituto Agronômico de Campinas (IAC) in Sao Paulo, Brazil. Its parentage was recorded as IAC 405-6 (Moscatel Rosado de Argentina × *Vitis "smalliana"* staminate) × IAC 570-2 (*v. tiliifolia* × Golden Queen). On-site identification of the above mentioned species indicates the "smalliana" is really a form of *V. caribaea* (synonym of *V. tiliifolia*). Berries of IAC 823-47 are red-black, small medium, ovoid, seedy, acidic, and loose in large clusters. Fruit quality is poor.

Esperanza is a self-fertile tropical hybrid grape variety selected by Francisco Watlington in Aibonito, Puerto Rico from the 1966 hand pollination of a native *V. caribaea* female with pollen of Lakemont, a seedless white Labruscana hybrid from the New York State Agricultural Experiment Station in Geneva. Esperanza produces fair quality, medium size, blue-black, seedy berries in well-filled medium to large clusters. The variety has been distributed widely without proprietary restrictions. IAC 823-47 is available from the IAC for breeding purposes.

SUMMARY OF THE INVENTION

A new and distinct variety of grapevine named Valplatinta was originated from a hand pollinated cross of IAC 823-47 (non-patented) by Esperanza (non-patented), made in 1973 in my private vineyard and nursery at Aibonito, Pureto Rico. A self-fertile seedling designated W73D-6 was eventually selected as the best of six siblings from a large propeny obtained from approximately 1,000 seeds.

W73D-6, which I have definitively named Valplatinta, was propagated by hardwood cuttings and tested at various locations throughout the island and abroad. In 1979 a test planting was established at the Rama Caida viticultural experiment station in Argentina, and in 1984 in the Leesburg, Fla. viticultural research program collection. Trials outside Pureto Rico have confirmed local recognition of the viticultural and enological attributes of the new variety, and also revealed its adaptation to a wide range of geographical environments.

Vines of Valplatinta are moderately vigorous, healthy and productive of commercial-quality grapes for juice and wine-making under tropical and subtropical conditions, for which few adequate cultivars are available. The adaptational characteristics of this new variety approach those of its *Vitis caribaea* ancestors. Its overall appearance and fruit attributes reflect a desirable integration of the native wild Caribbean grape and non-tropical cultivars of European (*V. vinifera*) and American (Labruscana) grapes. Valplatinta has retained the vegetative and fruit characteristics of the original hybrid vine in the course of asexual propagation over the years, in widely separate locations.

BRIEF DESCRIPTION OF THE SEVERAL VIEWS OF THE DRAWINGS

The accompanying photographs show typical specimens of the fruit and leaves of the new variety in color as nearly true as it is reasonably possible to render wherein.

DETAILED BOTANICAL DESCRIPTION

Figure 1:
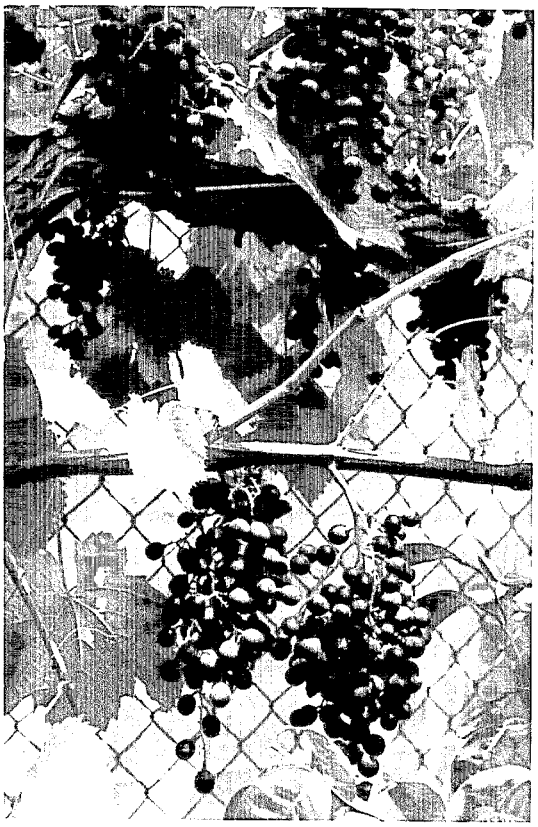
FIG. 1 is a color photograph of the invention showing fruit clusters, vine parts and details of underside of foliage.
Figure 2:
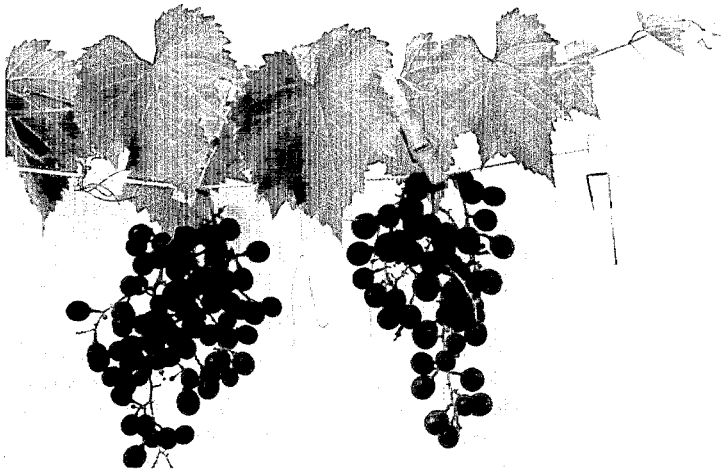
FIG. 2 is a color photograph showing fruit clusters juxtaposed with an extended cane featuring the upper side of foliage.
Figure 3:
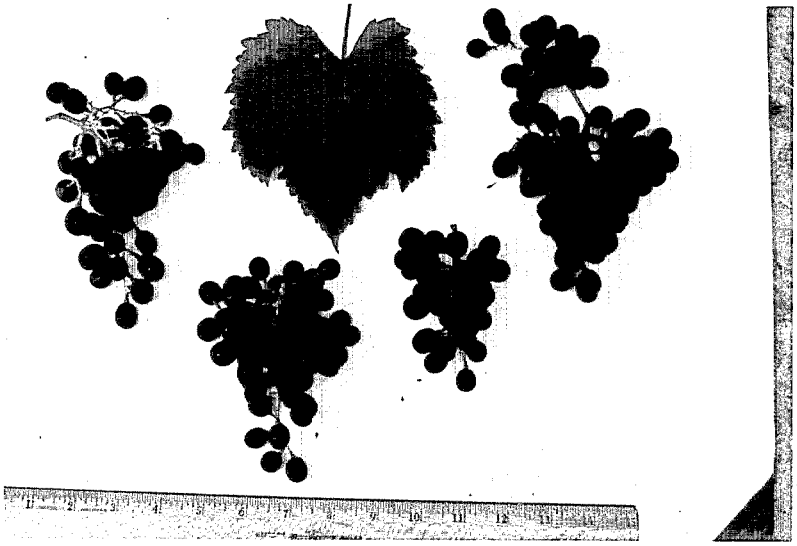
FIG. 3 is a color photograph which includes a 12 inch scale showing the relative sizes of berries, clusters and a mature leaf of the invention.

The following is a detailed botanical description of the pomological characteristics of this new grapevine variety. Color terminology is in accordance with that of The Royal Horticultural Society Colour chart (1966, London). Where dimensions, sizes, colors, and other characteristics are given, it is understood that the same are approximations of averages set forth as accurately as practicable. The description is taken from specimens grown at various tests sites, on their own roots, in Pureto Rico.

Vine:

*Canes.*—New growth lightly cobwebby becoming glabrous with age. Color purple (Greyed Purple Group 184) on side receiving sun, turning to yellow green (Yellow Green Group 145A-B) with nodes remaining purple, and maturing uniformly through orange to brown (Greyed Orange Group 164D to A).

*Foliage.*—Expanding leaves translucent suffused with purple (Greyed Purple Group 184–185) on yellow green ground color (Yellow Green Group 145A-B) giving bronzed appearance. Mature leaves green varying in shade according to nutrition and age (Green Group 136C, 139C; underside 136D, 139D). Visual contrast between top and bottom surfaces of leaves is slight. Underside is somewhat paler. Petiole, basal portion of five principal veins and proximal junctures with main veins tinted purple (Greyed Purple Group 184A-D). Outline of leaves broadly cuneiform to cordiform, with U-shaped petiolar sinus. Mid vein and superior lateral veins terminate in somewhat elongate points; rest of dentation slightly convex. Inferior lobes almost indistinct, superior lobes distinct but not pronounced, drooping; apex prominent cuneiform. Overall, mature leaf blade slightly concave and slightly longer than widest dimension, relatively thin and smooth textured with no visible pubescence, underside texture lightly sandy. Leaf size quite variable.

Fruit:

*Size and shape.*—Large medium, ellipsoid. Diameters, 1.5 cm (girth) by 1.8 cm (axial). Weight 2 g.

*Ripening and color.*—Ripens and colors evenly; full color at maturity dark blue-black with light bloom (Blue Group 103A-D).

*Seeds.*—Small medium, 6 mm long by 4 mm wide, light to dark brown in color, 2.5 per berry, weight 0.05 g/seed. Form obovate with rather flattened dorsal and ventral surfaces; beak small but sharp and distinct. Raphe thin and prominent on ventral surface, losing distinctness on convergence with depressed ovate to amygdaloid chalaza; chalaza 2 mm long by 1 mm wide, centered slightly above midsection of seed; ventral depressions well developed, abutting raphe.

*Skin and pulp.*—Skin medium thick, highly pigmented, adherent to clear, greenish and juicy pulp, sweet with slight tartness. Flavor neutral and uniform throughout berry. Color of juice next to skin, and fermented on skin red (Red Group 53).

*Sugar and acid.*—Sugar 19%, total acidity 1%, PH 3.3.

*Clusters.*—Long-conical, medium, 18 cm without stem; loose, weighing 250 g per full-size cluster. Three clusters per fruiting cane, up to 100 berries per cluster.

Phenology

The complete productive cycle of Valplatinta averages 135 days (plus or minus 5 days) from pruning to fruit harvest. Blooming takes place, on average, 30 days after pruning. Daylengths of 12 hours or over are required for adequate fruit-bud induction, expression (flowering) and sustained vegetative development. In Venezuela where extensive comparative studies of grape phenology have been carried out, varieties with similar cycles are considered "late".

Training, Pruning and Productivity

Valplatinta on its own roots is a vine of normal vigor with recumbent canes and a leafy canopy. It can be trained to any convenient trellis system, whether overhead, horizontal or vertical (fan). It responds well to spur pruning, the only technique that has proven practical in the tropics. An average of three clusters of fruit weighing a total of 500 g to 1,000 g (1 to 2 lbs) per can is produced from most buds on two or three-bud spurs.

Limited testing indicates that Valplatinta is amenable to double cropping (two crops in one year) as practiced in more equatorial zones (i.e. Venezuela at lat. 10° N). However, in Puerto Rico (lat. 18° 30′ N) climatic constraints make more advisable a system of double pruning to obtain a single crop of adequate quality. Foundation pruning is performed from mid June to mid July for optimal fruit induction under long days. Canes are pruned to single-bud spurs and all flower clusters removed from emerging new growth. Subsequently, production pruning is done from mid January to mid February, allowing normal two or three-bud spurs. The grapes are harvested from mid June to mid July.

Valplatinta is moderately productive. A mature two year old vine (trunk diameter about 3 by 4 cm) will yield over 6 kilograms of graps (14 to 15 lbs.) per crop. At a usual planting density of 6 meters square per vine, the yield would be roughly 4.5 tons per acre. Bearing size is attained in one year from cutting.

Other Characteristics

The invention combines desirable pomological characteristics for grapes grown under tropical conditions. It will grow and fruit adequately under relatively short growing season daylengths that prevail in the tropics. The fruit ripens and colors evenly, even when day and night-time temperatures are uniformly high. It yields must of appropriate acid/sugar ratio for juice and wine, and intensity of color for the same uses, also despite a continuously high temperature regime. The fruit is resistant to cracking and rotting in wet weather. Valplatinta is particularly useful as a teinturier because of its intense and stable pigmentation, which can, for example, turn a pale golden juice or wine ruby red (Red Group 46) in a dilution of one in four. The vine foliage has shown superior resistance to anthracnose and other fungus maladies in hot-humid tropical environments.

I claim:

1. A new and distinct variety of of grapevine, substantially as described and illustrated, characterized by its exceptional adaptation to tropical and subtropical environments, including superior resistance to common grape fungus pathogens, and unique usefulness for winemaking under such conditions.

* * * * *